(12) United States Patent
Hoeksel et al.

(10) Patent No.: US 7,090,644 B2
(45) Date of Patent: *Aug. 15, 2006

(54) DEVICE FOR DETERMINING A CHARACTERISTIC POINT IN THE CARDIAC CYCLE

(75) Inventors: Sebastiaan Adrianus Alphonsus Petrus Hoeksel, Maastricht (NL); Johannes Jacobus Schreuder, Bemelen (NL); Josef Reinier Cornelus Jansen, Noordwijkerhout (NL)

(73) Assignee: Arrow International Investment Corp., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/069,585

(22) Filed: Mar. 1, 2005

(65) Prior Publication Data

US 2005/0197584 A1 Sep. 8, 2005

Related U.S. Application Data

(63) Continuation of application No. 10/408,767, filed on Apr. 7, 2003, now Pat. No. 6,887,206, which is a continuation of application No. 09/863,075, filed on May 22, 2001, now Pat. No. 6,569,103, which is a continuation of application No. 09/091,325, filed as application No. PCT/NL96/00490 on Dec. 20, 1996, now Pat. No. 6,258,035.

(30) Foreign Application Priority Data

Dec. 22, 1995 (NL) .................................... 1001979

(51) Int. Cl.
*A61B 5/02* (2006.01)
*A61N 1/362* (2006.01)

(52) U.S. Cl. ...................... 600/481; 600/485; 600/500; 600/18

(58) Field of Classification Search ................ 600/481, 600/485, 486, 508, 509, 17, 18, 513, 521; 604/118, 913, 914

See application file for complete search history.

(56) References Cited

U.S. PATENT DOCUMENTS

| 3,965,339 A | 6/1976 | Mount et al. |
| 4,692,148 A | 9/1987 | Kantrowitz et al. |

(Continued)

FOREIGN PATENT DOCUMENTS

WO    WO 92/12669    8/1992

OTHER PUBLICATIONS

Luisada, A.A. et al. On the function of aortic valve and the mechanism of the first and second sounds. Japanese Heart Journal, vol. 18(1), Jan. 1977, pp. 81-91.

(Continued)

*Primary Examiner*—Robert L. Nasser
*Assistant Examiner*—Navin Natnithithadha
(74) *Attorney, Agent, or Firm*—Amster, Rothstein & Ebenstein LLP

(57) ABSTRACT

The present invention relates to a device for determining a characteristic point in the cardiac cycle that comprises means for calculating the curve of the blood flow rate D(t) in the aorta from the curve of the arterial blood pressure signal P(t) and determining from the curve of the blood flow rate D(t) in each cardiac cycle the time at which an incisura point lies. The device can be used for activating an intra-aortic balloon pump (IABP).

7 Claims, 4 Drawing Sheets

U.S. PATENT DOCUMENTS

| | | | |
|---|---|---|---|
| 4,697,574 | A | 10/1987 | Karcher et al. |
| 4,809,681 | A | 3/1989 | Kantrowitz et al. |
| 5,169,379 | A | 12/1992 | Freed et al. |
| 5,265,011 | A | 11/1993 | O'Rouke |
| 5,365,933 | A | 11/1994 | Elghazzawi |
| 5,390,679 | A | 2/1995 | Martin |
| 5,882,311 | A | 3/1999 | O'Rouke |
| 6,010,457 | A | 1/2000 | O'Rouke |
| 6,258,035 | B1 | 7/2001 | Hoeksel et al. |
| 6,569,103 | B1 | 5/2003 | Hoeksel et al. |

OTHER PUBLICATIONS

Eidenvall, Lars, et al., entitled "Information in the Aortic Blood Velocity Signal—A Simulation Study," Annual International Conference of the IEEE Engineering in Medicine and Biology Society, vol. 13, No. 5, 1991, pp. 2248-2249.

Portaluppi, F., et al., entitled "Transmission Delays of Different Portions of the Arterial Pulse—A Comparison Between the Indirect Aortic and Carotid Pulse Tracings," Acta Cardiologica, vol. 38, No. 1, 1983, pp. 49-59.

DEVICE FOR DETERMINING A CHARACTERISTIC POINT IN THE CARDIAC CYCLE

CROSS-REFERENCE TO RELATED APPLICATIONS

This application is a continuation of U.S. application Ser. No. 10/408,767, filed Apr. 7, 2003, now U.S. Pat. No. 6,887,206, which is a continuation of U.S. application Ser. No. 09/863,075, filed May 22, 2001, now U.S. Pat. No. 6,569,103 B2, which is a continuation of U.S. application Ser. No. 09/091,325, filed Jun. 21, 1999, now U.S. Pat. No. 6,258,035 B1, which is a U.S. National Phase of PCT Application No. PCT/NL96/00490, filed Dec. 20, 1996, which claims priority to NL Application No. 1001979, filed Dec. 22, 1995, the contents of all of which are hereby incorporated by reference.

The invention relates to a device for determining a characteristic point in the cardiac cycle. Such a device can be used for, for example, activating an intra-aortal balloon pump (IABP).

An IABP contains, inter alia, an intra-aortal balloon (IAB), which can be inserted, for example, into the aorta of a patient with a poorly functioning heart, and a pumping device.

In each cardiac cycle the IAB is inflated by means of the pumping device after the end of an ejection phase of the left ventricle of the heart, and is deflated again before the commencement of the following ejection phase.

The pumping action of the heart is improved in this way, and there is an improvement in the blood supply to the coronary artery.

For good functioning of the IABP it is of great importance for the IAB to be inflated and deflated at the correct times in the cardiac cycle. In particular, the correct choice of the time at which the IAB is inflated is of very great importance.

If the IAB is inflated too soon, the pumping action of the heart is reinforced to a lesser extent, or the pumping action can even be adversely affected, because the prematurely inflated IAB causes a flow resistance in the aorta during the ejection of the left ventricle which is still occurring at the time.

If the time selected is too late, the functioning of the IABP is also less effective. A lower volume of blood is then pumped through the IAB, and the coronary artery and the vascular bed undergo a high perfusion pressure for only a short period of time.

The times for inflating and deflating the IAB can be set manually by an experienced person at fixed times in the cardiac cycle on the basis of the electro-cardiogram (ECG) of the heart. A disadvantage of this is that when there is a gradual acceleration or slowing-down of the cardiac cycle the set times deviate increasingly from the desired times, and therefore have to be reset repeatedly. It is also impossible to make allowances for an irregular cardiac cycle, and in particular the setting of the time at which the IAB is inflated is not performed sufficiently accurately.

The end of the ejection phase and the accompanying closure of the aortic valve are themselves indicated accurately by the occurrence of a dip in the arterial blood pressure signal P(t). This dip is also known as the incisura point.

U.S. Pat. No. 5,183,051 discloses a device by means of which an attempt is made to determine the incisura point by looking for the dip in the curve of the arterial blood pressure signal P(t) within a previously defined period of time. However, the period of time may be incorrectly defined and, besides, the device does not work in the case of a damped blood pressure signal, because in that case the incisura point is not accompanied by a clear blood pressure change.

A further disadvantage of this device is that it is still not possible to make allowance for an irregular cardiac cycle, while patients in whom an IABP is used generally have an irregular cardiac cycle. Moreover, the use of the device for activating an IABP is not mentioned at all in U.S. Pat. No. 5,183,051.

A device which detects the incisura point in the curve of the arterial blood pressure signal P(t) is proposed in IEEE Transactions on Biomedical Engineering 1990, 37(2), pp. 182–192. However, it is possible that this device may interpret irregularities in the curve of the arterial blood pressure signal as the incisura point, which upsets the functioning of the IABP.

U.S. Pat. No. 4,809,681 discloses a device for activating an IABP which determines from the ECG the point at which the IAB must be deflated. However, it is not possible to determine the incisura point using the device.

Sakamoto et al., ASAIO Journal 1995, pp. 79–83, discloses a device which forecasts the position of the incisura point in a cardiac cycle from the ECG by calculating the length of the ejection phase from the period of time of the previous heartbeat. This device is still inaccurate.

SUMMARY OF THE INVENTION

The object of the invention is to provide a device for determining a characteristic point in the cardiac cycle which does not have the above-mentioned disadvantages.

Surprisingly, this is achieved by the fact that the device according to the invention comprises means for calculating the curve of the blood flow rate D(t) in the aorta from the curve of the arterial blood pressure signal P(t) and determining the time (ti) at which the incisura point lies from the curve of the blood flow rate D(t) in each cardiac cycle.

The time at which the incisura point lies can be determined instantaneously from the curve of D(t), so that the moment the incisura point is reached in a cardiac cycle the IABP can be activated by the device at precisely the correct moment (in real time).

A further advantage of the device according to the invention is that only the curve of the arterial blood pressure need be measured, which is a simple procedure.

The device according to the invention can be used for many purposes. For instance, the device is suitable for use in activating heart-function-supporting equipment. The device is preferably used for activating an IABP. It is also possible to use the device as part of a monitoring system which determines the duration of the ejection phase of a heartbeat and relates the latter to the total period of the heartbeat. The haemodynamic condition of a patient can be followed using such a monitoring system. This can be carried out starting from the arterial blood pressure signal or from the pulmonic blood pressure signal.

The device preferably has means for delivering a signal at the moment when the incisura point is reached. By means of said signal, the IABP, for example, is put into operation in order to inflate the IAB. The means which the device according to the invention comprises for calculating the curve of the blood flow rate D(t) from the curve of the arterial blood pressure signal P(t) can be a calculating device, for example a computer, a microprocessor or a digital calculating machine. The calculating device in this case is loaded with a calculation program for calculating the blood flow rate D(t) from the arterial blood pressure signal P(t).

The calculation program can be based on one of the models known to the person skilled in the art for calculating the blood flow rate D(t) from the arterial blood pressure signal P(t).

Examples of such models are given in IEEE Transactions on Biomedical Engineering 1985, 32(2), pp. 174–176, Am. J. Physiol. 1988, 255 (Heart Circ. Physiol.), H742–H753 and in WO 92/12669.

Very good results are obtained if the calculation program is based on the Windkessel model, as also described in the abovementioned literature. In a suitable embodiment the Windkessel model is based on three elements, namely a characteristic input resistance, Rao, an arterial compliance, Cw, and a peripheral resistance, Rp.

The characteristic input resistance, Rao, represents the flow resistance experienced by the heart. The arterial compliance, Cw, represents the ability of the aorta and the arteries to store a particular volume of blood as the result of elastic expansion. The peripheral resistance, Rp, represents the resistance of the vascular bed.

The values used for the elements in the Wind-kessel model are known from the literature. Suitable values are known from, for example, Am. J. Physiol. 1988, 255 (Heart Circ Physiol.), H742–H753.

Very good results are achieved if account is taken of the dependence of the elasticity of the aorta on the current blood pressure, as described in WO 92/12669.

An advantage of the calculation program based on the Windkessel model is that the values for the elements in the model used in the calculation do influence the absolute value of the calculated blood flow rate, but the position of the incisura point depends only to a very small extent on the values used for the elements. It is therefore not necessary to know the values of the elements very well for a particular patient in order to obtain good results from the calculation of the incisura point.

The position of the incisura point can be determined very accurately from the curve of the blood flow rate D(t) calculated in this way, while said point is difficult to determine from the curve of the arterial blood pressure signal P(t).

It is therefore possible for the first local minimum which occurs in the curve of the blood flow rate D(t) after the beginning of the injection phase of the left ventricle to be determined. This point represents the incisura point.

The minimum in the blood flow rate D(t) can be determined according to one of the calculation methods known for it. For instance, it is possible in each case to compare three successive values in the curve of the blood flow rate D(t) with each other. If the condition D(t−dt)>D(t)<D(T+dt) is met, the minimum is reached at time t. If dt is selected at a sufficiently low level, the minimum can actually be detected virtually at the moment when it is reached, and at that moment a signal can be generated and supplied to the IABP. It is preferable for dt to be less than 0.02 second, more preferably less than 0.01 second, and still more preferably less than 0.005 second.

Even more accurate results are obtained if the occurrence of the local minimum is also subject to the condition that at the moment when the local minimum is reached the blood flow rate is situated below a specific threshold value Dd. This ensures that reflections in the blood pressure signal which can occur during the ejection phase of the left heart ventricle are not detected as the incisura point. The threshold value can be equal to, for example, 10% of the value of the blood flow rate, while the blood flow rate from the left ventricle has reached its maximum value. The calculation program can be set up in such a way that the threshold value is recalculated after each cardiac cycle. The threshold value is preferably selected so that it is equal to zero, Dd=0. This threshold value is reached just before the incisura point occurs, so that the chance of a reflection being detected wrongly as an incisura point is very small.

In order to obtain an accurate calculation of D(t) when the latter is just above the zero value, it is important to know the correct value for Rp. This value can also be calculated from Rao and Cw using the Windkessel model, by assuming that the total quantity of blood which flows into the Windkessel compliance in a heartbeat, or even taken over a number of heartbeats, also flows out of it again. Rao and Cw as such can be estimated accurately for a patient if sex and age are known.

It is also possible for the incisura point to be determined at the time that D(t)=0, after the beginning of the ejection phase. This ensures that a signal can already be given to the IABP just before the aorta valves close, and if an inertia occurs during the inflation of the IAB, the IAB can be inflated when the valves are actually closing.

The beginning of the ejection phase of the left heart ventricle can be determined from the ECG, from the curve of the arterial blood pressure signal P(t), or from a combination of the two. The way in which this can be carried out is known to the person skilled in the art.

The time at which the beginning of the ejection phase is reached can be transmitted to the device according to the invention, which uses the time to activate the device according to the invention for the calculation of the next incisura point. A signal for deflating the IABP can also be supplied at that time to the IABP.

A yet further improved device according to the invention is obtained if the device has a filter for filtering high-frequency noise out of the blood pressure signal.

This ensures that irregularities in the curve of the blood pressure signal are filtered out, with the result that the chance of the device detecting the incisura point at an incorrect time is reduced even further. This is important in particular if the device has to function in an environment where its proper functioning can be interfered with by the frequent occurrence of electromagnetic waves.

The device according to the invention is preferably connected to a pressure recorder for measuring the arterial blood pressure, which pressure recorder is attached to the IAB. In this way a blood pressure signal P(t) is supplied to the device and is measured in the aorta, directly behind the heart. This reduces even further the chance of the blood pressure signal having irregularities which are incorrectly identified by the device as an incisura point. Another advantage of this is that the measured pressure signal is slowed down little, if at all, but properly reflects the current stage of the cardiac cycle.

The invention is explained in greater detail with reference to the drawing, without being restricted thereto.

DETAILED DESCRIPTION OF THE INVENTION

Figure 1:
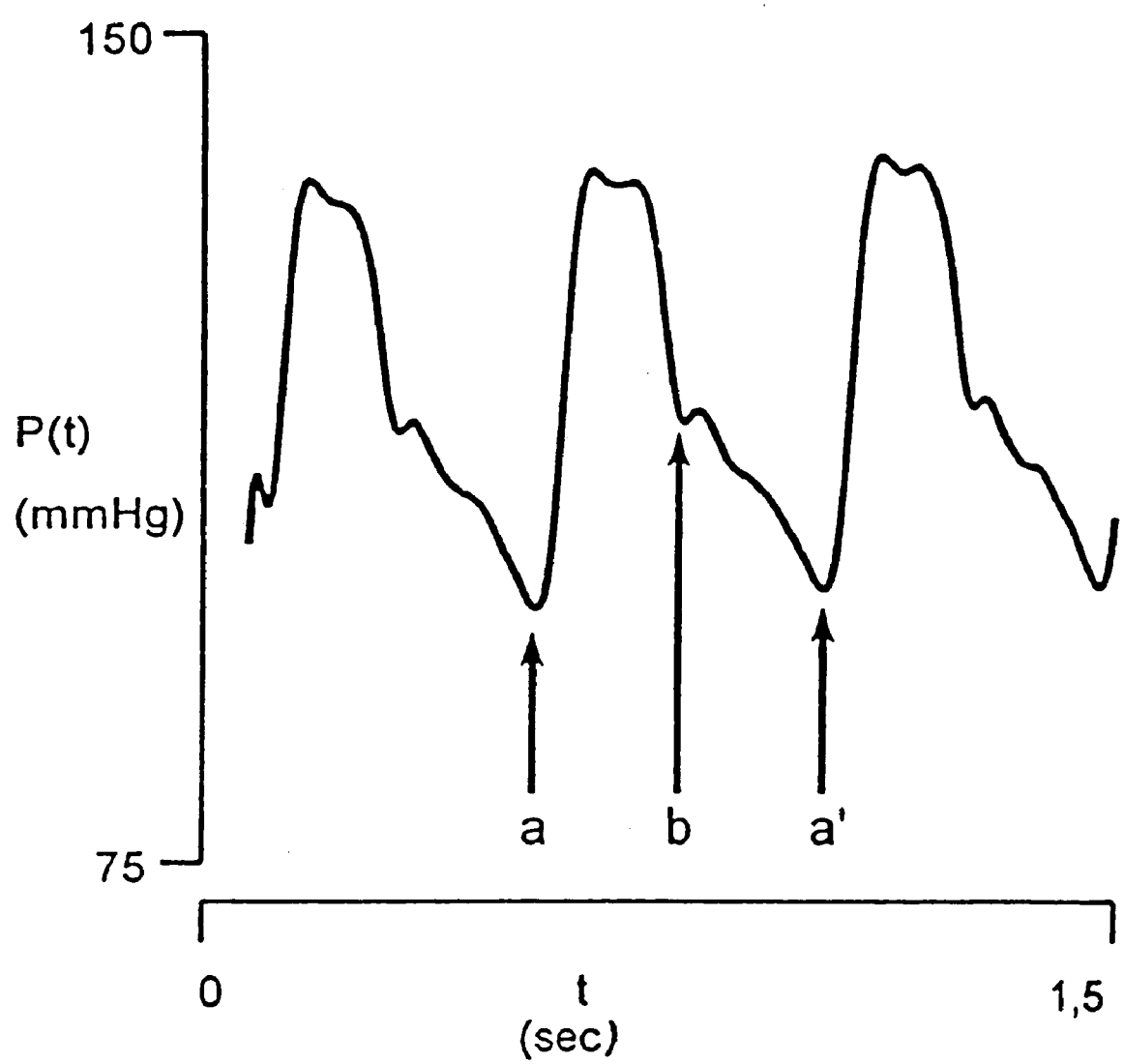
FIG. 1 gives an example of the curve of a measured arterial blood pressure P(t). P(t) is plotted in millimeters mercury pressure (mmHg) on the y-axis, and the time t is plotted in seconds (sec) on the x-axis.

In FIG. 1 the time a in the curve of the arterial blood pressure signal P(t) is the point at which an ejection phase of the left ventricle begins. This is the time at which the IAB must be deflated. Further, at this time a signal can be supplied to the device according to the invention, in order to start up a calculation cycle for determining the typical point in the cardiac cycle. The time a can be determined from the ECG, from the arterial blood pressure signal P(t), or from both.

The time b is the time at which the incisura point is reached and the heart valves close. This is the time at which the IAB must be inflated. It can be seen clearly that the incisura point is manifested only in the form of an unsharp local minimum in the curve of the arterial blood pressure signal P(t).

At the time a' the cardiac cycle ends, and the ejection phase of the following cardiac cycle begins. The time interval a–b is also known as the systolic phase. The time interval b–a' is also known as the diastolic phase.

Figure 2:
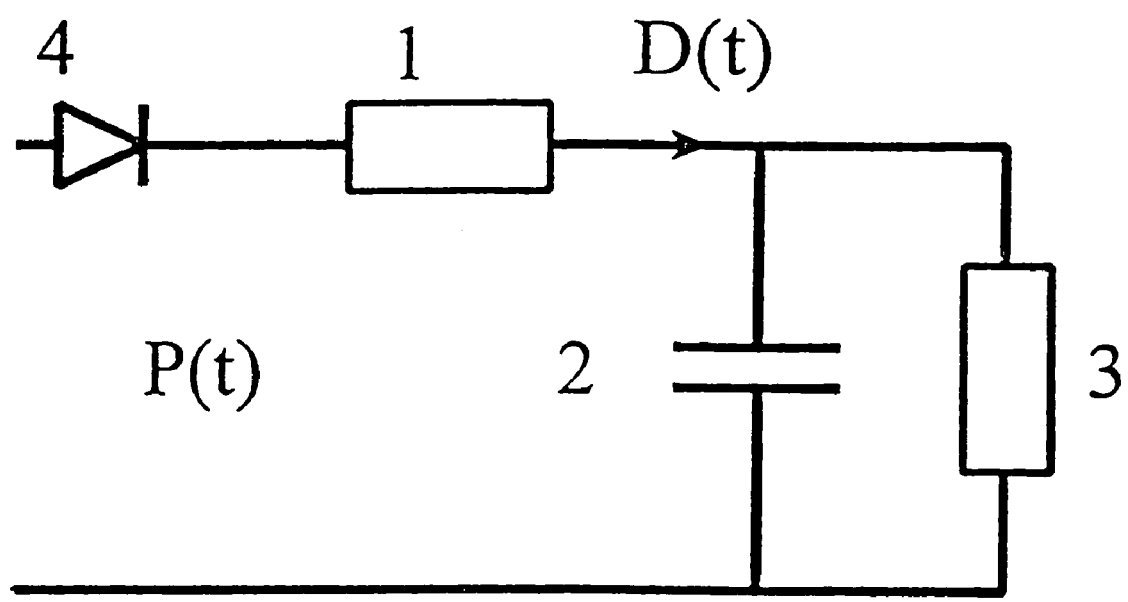
FIG. 2 shows a diagram of a Windkessel model.

FIG. 2 gives a diagram of a simple Windkessel model containing the following elements: a characteristic input resistance, Rao (1), an arterial compliance, Cw (2), and a peripheral resistance, Rp (3). Further, the aorta valves are modelled by means of an ideal diode (4) which closes after D(t) becomes negative in a cardiac cycle.

Figure 3:
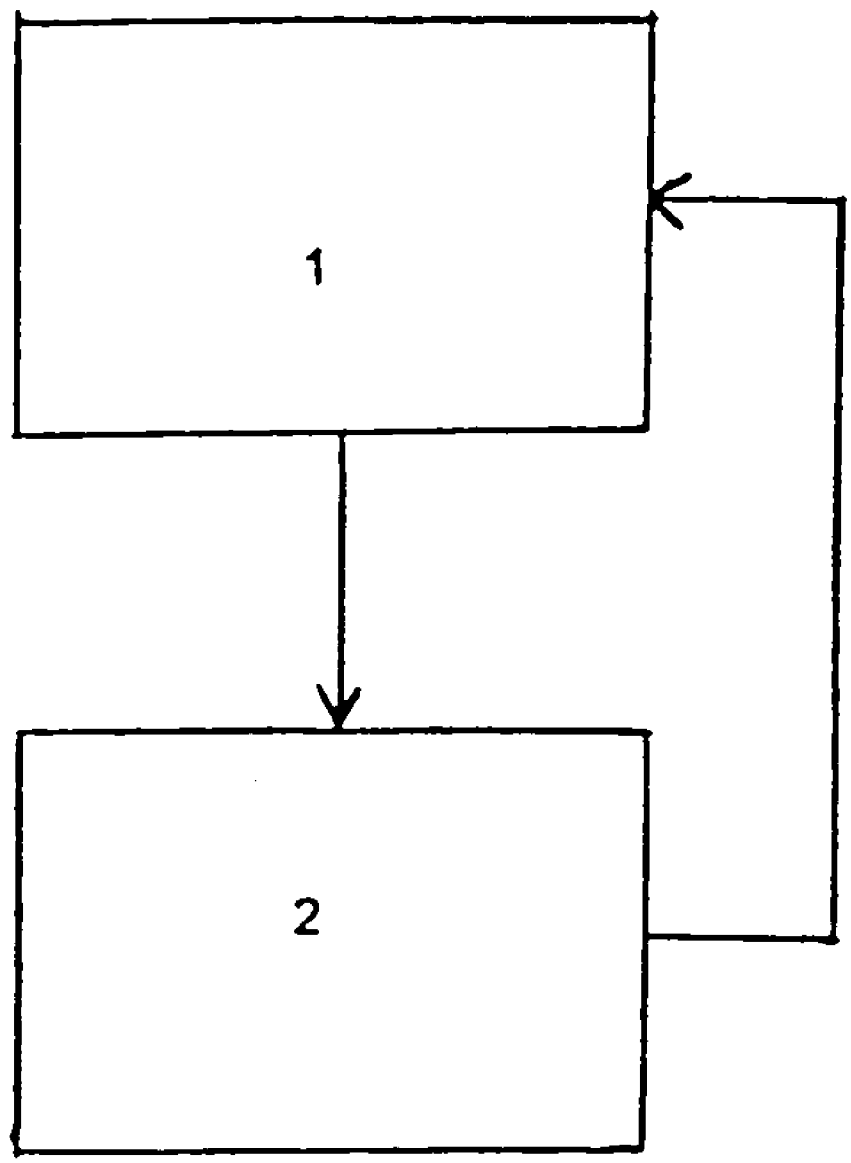
FIG. 3 gives a diagram of a calculation program for calculating the curve of the blood flow rate D(t) from the curve of the arterial blood pressure signal P(t), based on the Windkessel model of FIG. 2.

FIG. 3 gives a diagram for a calculation program for calculating the incisura point.

In step 1, indicated by (1) in FIG. 3, the beginning of the ejection phase (point a) is detected, for example from the ECG. So long as the beginning of the ejection phase has not yet been detected, D(t)=0 is assumed. If the beginning of the ejection phase is detected, one proceeds to step 2 (2).

During step 2 the curve of the blood flow rate D(t) is calculated from the measured pressure signal P(t), for example by means of the equation:

$$(1+Rao/Rp) \cdot Iao + Rao \cdot Cw \cdot \dot{I}ao = Pao/Rp + Cw \cdot \dot{P}ao$$

($\dot{I}ao$ and $\dot{P}ao$ are the first-order derivatives according to time of $Iao$ and $Pao$).

As soon as D(t)<0 the program starts to look for the first local minimum in the D(t), for example by in each case comparing a series of at least three successive points in the curve of D(t).

When the first local minimum, the incisura point, is reached, a signal is sent to the IABP, and step 1 (1) starts again.

Figure 4:
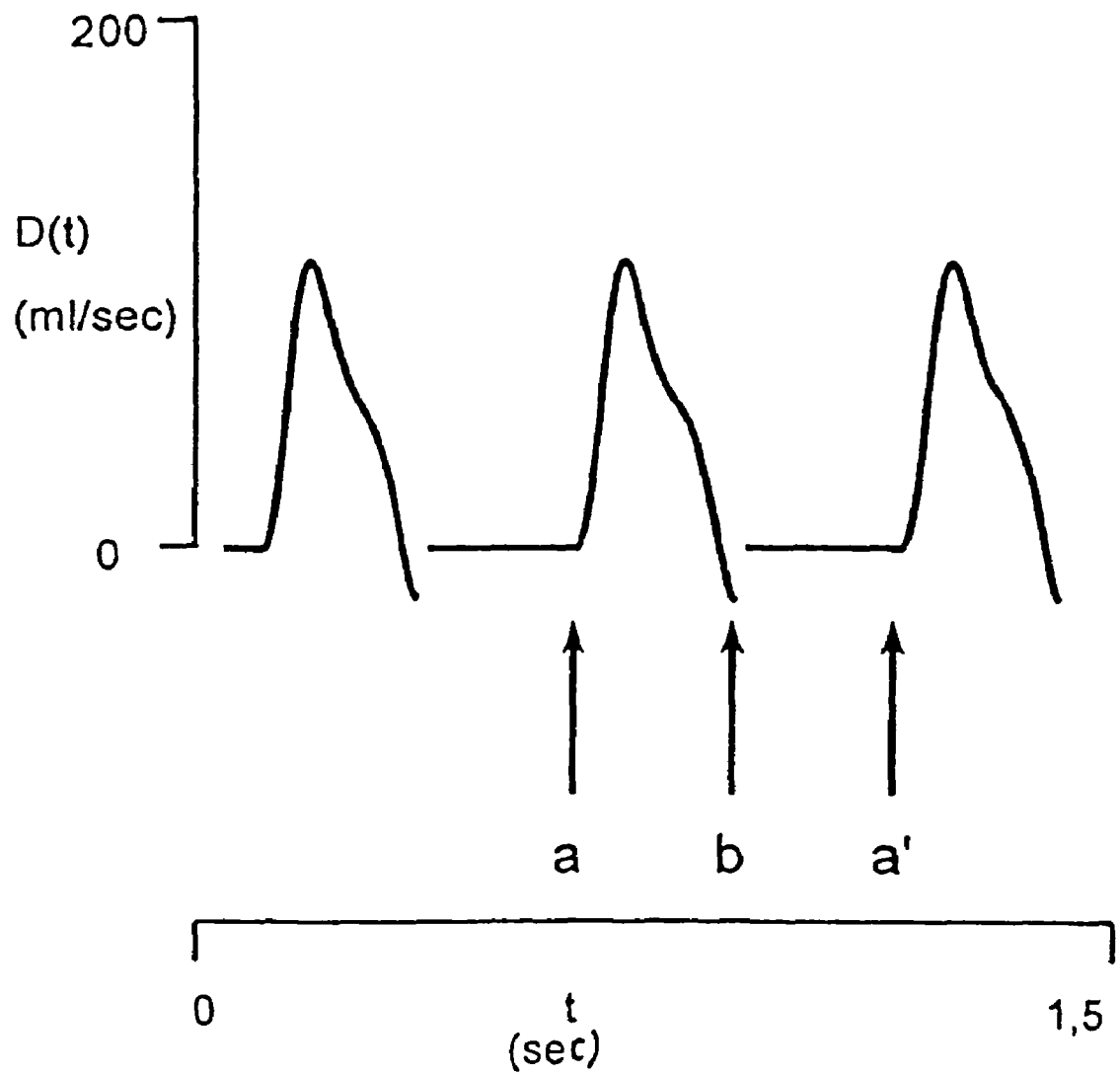
FIG. 4 gives the curve of the blood flow rate D(t) calculated from the curve of the measured arterial blood pressure signal P(t) according to FIG. 1, using the calculation program from FIG. 3. D(t) is plotted in milliliters per second (ml/sec) on the y-axis, and the time is again plotted on the x-axis.

From the curve of the blood flow rate in FIG. 4, calculated from the curve of the arterial blood pressure signal according to FIG. 1 by means of the calculation program from FIG. 3, the incisura point can be seen clearly as a sharp local minimum.

The diode (4) from FIG. 2 makes D(t) equal to zero during the diastolic phase.

The invention claimed is:

1. A method for activating an intra-aortal balloon pump (IABP) comprising:
    (a) calculating the curve of the blood flow rate D(t) in the aorta from the curve of the arterial blood pressure signal P(t) and determining from the curve of the blood flow rate D(t) in each cardiac cycle the time at which an incisura point lies, wherein the incisura point is determined from a first local minimum in the curve of the blood flow rate D(t) after the beginning of an ejection phase;
    (b) delivering a first signal when the incisura point is reached, wherein said first signal activates an intra-aortal balloon pump (IABP) to inflate; and
    (c) delivering a second signal at the beginning of the ejection phase, wherein said second signal activates an intra-aortal balloon pump (IABP) to deflate.

2. The method according to claim 1, wherein the blood flow rate D(t) lies below a threshold value Dd.

3. The method according to claim 2, wherein Dd is equal to 10% of the blood flow rate when the blood flow rate from the left ventricle has reached its maximum value.

4. The method according to claim 2, wherein Dd=0.

5. The method according to claim 1, wherein the incisura point is determined when D(t)=0 after the beginning of an ejection phase.

6. The method according to claim 1, which further comprises filtering out a high-frequency noise on the arterial blood pressure signal P(t).

7. The method according to claim 1, wherein calculation of the curve of the blood flow rate D(t) in the aorta from the curve of the arterial blood pressure signal P(t) is based on the Windkessel model.

\* \* \* \* \*